(12) United States Patent  (10) Patent No.: US 8,722,067 B2
Wang et al.  (45) Date of Patent: *May 13, 2014

(54) METHOD FOR SILK FIBROIN GELATION USING SONICATION

(75) Inventors: Xiaoqin Wang, Winchester, MA (US); Jon Kluge, Southborough, MA (US); Gary G. Leisk, Wilmington, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/457,705

(22) Filed: Apr. 27, 2012

(65) Prior Publication Data

US 2013/0060008 A1  Mar. 7, 2013

Related U.S. Application Data

(63) Continuation of application No. 12/601,845, filed as application No. PCT/US2008/065076 on May 29, 2008, now Pat. No. 8,187,616.

(60) Provisional application No. 60/940,554, filed on May 29, 2007.

(51) Int. Cl.
*A61K 9/00* (2006.01)
*A61K 38/17* (2006.01)

(52) U.S. Cl.
USPC .......................................... 424/400; 530/353

(58) Field of Classification Search
None
See application file for complete search history.

(56) References Cited

U.S. PATENT DOCUMENTS

| | | |
|---|---|---|
| 1,989,005 A | 1/1935 | Fink et al. |
| 4,233,212 A | 11/1980 | Otoi et al. |
| 4,325,741 A | 4/1982 | Otoi et al. |
| 4,798,722 A | 1/1989 | Edman et al. |
| 4,820,418 A | 4/1989 | Hirotsu et al. |
| 5,047,507 A | 9/1991 | Buchegger et al. |
| 5,290,494 A | 3/1994 | Coombes et al. |
| 5,606,019 A | 2/1997 | Cappello |
| 5,728,810 A | 3/1998 | Lewis et al. |
| 5,770,193 A | 6/1998 | Vacanti et al. |
| 5,932,462 A | 8/1999 | Harris et al. |
| 5,994,099 A | 11/1999 | Lewis et al. |
| 6,106,816 A | 8/2000 | Hitchen |
| 6,110,590 A | 8/2000 | Zarkoob et al. |
| 6,123,819 A | 9/2000 | Peeters |
| 6,175,053 B1 | 1/2001 | Tsubouchi |
| 6,592,623 B1 | 7/2003 | Bowlin et al. |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,780 B2 | 11/2010 | Kaplan et al. |
| 7,960,509 B2 | 6/2011 | Kaplan et al. |
| 8,071,722 B2 | 12/2011 | Kaplan et al. |
| 2002/0028243 A1 | 3/2002 | Masters |
| 2003/0007991 A1 | 1/2003 | Masters |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0147681 A1 | 7/2005 | Zhao |
| 2005/0260706 A1 | 11/2005 | Kaplan et al. |
| 2007/0187862 A1 | 8/2007 | Kaplan et al. |
| 2007/0212730 A1 | 9/2007 | Vepari et al. |
| 2008/0058400 A1 | 3/2008 | Yang et al. |
| 2008/0085272 A1 | 4/2008 | Kaplan et al. |
| 2008/0280360 A1 | 11/2008 | Kaplan et al. |
| 2008/0293919 A1 | 11/2008 | Kaplan et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |

(Continued)

FOREIGN PATENT DOCUMENTS

| | | |
|---|---|---|
| CA | 2405850 | 10/2002 |
| EP | 0361391 A2 | 4/1990 |
| EP | 1440088 | 5/2008 |
| GB | 1182153 | 2/1970 |
| JP | 55-139427 | 10/1980 |
| JP | 56166235 | 12/1981 |
| JP | 58-38449 | 8/1983 |
| JP | 60-142259 | 7/1985 |
| JP | 60-259677 | 12/1985 |
| JP | 01118544 | 11/1989 |

(Continued)

OTHER PUBLICATIONS

Certified Translation of JP 02-084503 (Minoura, N.), Mar. 26, 1990.*
Chen et al., "Rheological Characterization of Nephila Spidroin Solution", Biomacromolecules, 2002, vol. 3, pp. 644-648.*
Kim et al., "Structure and Properties of Silk Hydrogels", Biomacromolecules, 2004, vol. 5, pp. 786-792.*

(Continued)

*Primary Examiner* — Suzanne M Noakes
(74) *Attorney, Agent, or Firm* — Choate, Hall & Stewart, LLP

(57) ABSTRACT

This invention provides for a process of rapidly forming silk fibroin gelation through ultrasonication. Under the appropriate conditions, gelation can be controlled to occur within two hours after the ultrasonication treatment. Biological materials, including viable cells, or therapeutic agents can be encapsulated in the hydrogels formed from the process and be used as delivery vehicles.

20 Claims, 5 Drawing Sheets

(56) References Cited

U.S. PATENT DOCUMENTS

| | | |
|---|---|---|
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0292338 A1 | 11/2010 | Rheinnecker et al. |
| 2011/0046686 A1 | 2/2011 | Kaplan et al. |
| 2011/0076384 A1 | 3/2011 | Cannizzaro et al. |
| 2011/0105402 A1 | 5/2011 | Kim et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |
| 2012/0231499 A1 | 9/2012 | Lee et al. |

FOREIGN PATENT DOCUMENTS

| | | | |
|---|---|---|---|
| JP | 02-084503 | * | 3/1990 |
| JP | 02-084503 A | | 3/1990 |
| JP | 04-263611 | | 9/1992 |
| JP | 05163132 | | 6/1993 |
| JP | 06-346314 | | 12/1994 |
| JP | 08-295697 | | 11/1996 |
| JP | 10-36676 | | 2/1998 |
| JP | 2000-273264 | | 10/2000 |
| JP | 2003192807 | | 7/2003 |
| JP | 2004068161 | | 3/2004 |
| WO | 99/01089 | | 1/1999 |
| WO | 99/45964 A1 | | 9/1999 |
| WO | 01/36531 | | 5/2001 |
| WO | 01/56626 | | 8/2001 |
| WO | 02/072931 | | 9/2002 |
| WO | 03/022909 | | 3/2003 |
| WO | 03/038033 | | 5/2003 |
| WO | 2004/041845 | | 5/2004 |
| WO | 2004/000915 | | 12/2004 |
| WO | 2005/012606 | | 2/2005 |
| WO | 2005/012606 A2 | | 10/2005 |
| WO | 2005/123114 | | 12/2005 |
| WO | 2005/123114 A2 | | 12/2005 |
| WO | 2008/118113 A1 | | 2/2008 |
| WO | 2008/106485 A2 | | 4/2008 |
| WO | 2008/052755 A2 | | 5/2008 |
| WO | 2008/052775 A2 | | 5/2008 |
| WO | 2008/127401 A2 | | 10/2008 |
| WO | 2008/127405 | | 10/2008 |
| WO | 2009/153140 A2 | | 12/2009 |
| WO | 2009/156226 | | 12/2009 |
| WO | 2010/060600 A1 | | 6/2010 |
| WO | 2011/006133 | | 1/2011 |

OTHER PUBLICATIONS

Youmans, H.L., "Measurement of pH of distilled water", J. Chem. Educ., 1972, vol. 49, No. 6, p. 429.*
Agarwal et al., Journal of Applied Polymer Science, 63(3):401-410 (1997). "Effect of Moisture Absorption on the Thermal Properties of Bombyx mori Silk Fibroin Films".
Altman et al., Biomaterials, 23:4131-4141 (2002). "Silk matrix for tissue engineered anterior cruciate ligaments".
Altman et al., Biomaterials, 24:401-416 (2003). "Silk-based biomaterials".
Ando et al, Reports on Progress in Polymer Physics in Japan, XXIII:775-778 (1980). "Piezoelectric and Related properties of Hydrated Silk Fibroin".
Asakura et al., Macromolecules, 17:1075-1081 (1984). NMR of silk fibroin 2. 13C NMR study of the chain dynamics and solution structure of Bombyx mori silk fibroin.
Asakura et al., Macromolecules, 18:1841-1845 (1985). "Conformation Characterization of Bombyx Mori Silk Fibroin in the Solid State by High-Frequency 13C Cross Polarization-Magic Angle Spinning NMR, X-ray Diffraction, and Infrared Spectroscopy".
Bini et al., J. Mol. Biol., 335:27-40 (2004). "Mapping Domain Structures in Silks from Insects and Spiders Related to Protein Assembly.".
Cai et al., Int. J. Mol. Sci., 11:3529-3539 (2010). "Fabrication of Chitosan/Silk Fibroin Composite Nanofibers for Wound-dressing Applications".
Chao et al., J Biomed Mater Res B Appl Biomater., 95(1):84-90 Author Manuscript (2010). "Silk hydrogel for cartilage tissue engineering".
Chen et al., J Appl Polymer Sci, 65:2257-2262 (1997). "pH sensitivity and ion sensitivity of hydrogels based on complex-forming chitosan/silk fibroin interpenetrating polymer network".
Chen et al., J Appl Polymer Sci, 73:975-980 (1999). "Separation of alcohol-water mixture by pervaporation through a novel natural polymer blend membrane-chitosan/silk fibroin blend membrane—chitosan/silk fibroin blend membrane".
Chen et al., Biomacromolecules, 3:644-648 (2002). "Rheological Characterization of Nephila Spidroin Solution".
Chen et al., J Biomed Mater Res, 67A:559-570 (2003). "Human bone marrow stromal cell and ligament fibroblast responses on RGD-modified silk fibers".
Chen et al., Proteins: Structure, Function, and Bioinformatics, 68:223-231 (2007). "Conformation transition kinetics of Bombyx mori silk protein".
Demura et al., Biosensors, 4:361-372 (1989). "Immobilization of biocatalysts with Bombyx mori silk fibroin by several kinds of physical treatment and its application to glucose sensors".
Demura et al., J Membrane Science, 59:39-52 (1991). "Porous membrane of Bombyx mori silk fibroin: structure characterization, physical properties and application to glucose oxidase immobilization".
Derwent Record, Abstract of JP 08295697 A2 "Production of aqueous solution of silk fibroin at high concentration." Nov. 12, 1996.
Doshi et al. J Electrostatics, 35:151-160 (1995). "Electrospinning process and applications of electrospun fibers".
Freddi et al., J Appl Polymer Sci, 56:1537-1545 (1995). "Silk fibroin/cellulose blend films: preparation, structure, and physical properties".
Furst et al., Ann Thorac Surg, 79:1522-1529 (2005). "Release of Glutaraldehyde From an Albumin-Glutaraldehyde Tissue Adhesive Causes Significant In Vitro and In Vivo Toxicity".
Gill et al., Urology, 65:463-466 (2005). "Improved Hemostasis During Laparoscopic Partial Nephrectomy Using Gelatin Matrix Thrombin Sealant".
Hijirida et al., Biophysical Journal, 71:3442-3447 (1996). "13C NMR of Nephila clavipes major ampullate silk gland".
Hinman et al., TIBTECH, 18:374-379 (2000). "Synthetic spider silk: a modular fiber".
Hofmann et al., Journal of Controlled Release, 111:219-227 (2006). "Silk fibroin as an organic polymer for controlled drug delivery".
Horan et al., Biomaterials, 26:3385-3393 (2005). "In vitro degradation of silk fibroin".
Hu et al., Biomacromolecules, 12:1686-1696 (2011). "Regulation of Silk Material Structure by Temperature-Controlled Water Vapor Annealing".
Huang et al., J Biomater Sci Polymer Edn, 12(9):979-993 (2001). "Engineered collagen-PEO nanofibers and fabrics".
Huang et al., Macromolecules, 33:2989-2997 (2000). "Generation of synthetic elastin-mimetic small diameter fibers and fiber networks".
Jang et al., Oral Surg Oral Med Oral Pathol Oral Radio Endod, 109:831-836 (2010). "Restoration of peri-implant defects in immediate implant installations by Choukroun platelet-rich fibrin and silk fibroin powder combination graft".
Jenkins et al., Surgery, 20:124-132 (1946). "Clinical and Experimental Observations on the Use of Gelatin Sponge or Foam".
Jiang et al., Materials Letters, 60:919-925 (2006). "Tensile behavior and morphology of differently degummed silkworm (Bombyx mori) cocoon silk fibres".
Jin et al., Biomacromolecules, 3:1233-1239 (2002). "Electrospinning Bombyx mori silk with poly(ethylene oxide)".

(56) References Cited

OTHER PUBLICATIONS

Jin et al., Adv. Funct. Mater., 15:1241-1247 (2005). "Water-Stable Silk Films with Reduced β-Sheet Content".
Jin et al., Nature, 424:1057-1061 (2003). "Mechanism of silk processing in insects and spiders".
Kim et al., Biomacromolecules, 5:786-792 (2004). "Structure and Properties of Silk Hydrogels".
Kweon et al., J Appl Polymer Sci, 80:1848-1853 (2001). "Preparation of semi-interpenetrating polymer networks composed of silk fibroin and poly(ethylene glycol) macromer".
Lawrence et al., Biomaterials, 30(7):1299-1308 Author Manuscript (2009). "Silk film biomaterials for cornea tissue engineering".
Lazaris, Science, 295:472-476 (2002). "Spider silk fibers spun from soluble recombinant silk produced in mammalian cells".
Lee et al., Oral Surg Oral Med Oral Pathol Oral Radiol Endod, 109:e33-e38 (2010). "A combination graft of low-molecular-weight silk fibroin with Choukroun platelet-rich fibrin for rabbit calvarial defect".
Leisk et al., Adv. Mater., 22:711-715 (2010). "Electrogelation for Protein Adhesives".
Li et al., Biomaterials, 27:3115-3124 (2006). "Electrospun Silk-BMP-2 scaffolds for bone tissue engineering".
Li et al., J Mater Sci: Mater Med, 19:577-582 (2008). "Effect of silicon on the formation of silk fibroin/calcium phosphate composite".
Liang et al., J Appl Polymer Sci, 45:1937-1943 (1992). "Improvements of the physical properties of fibroin membranes with sodium alginate".
Lin et al., Pharmaceutical Research, 26(3):631-643 (2008). "PEG Hydrogels for the Controlled Release of Biomolecules in Regenerative Medicine".
Lowe et al., J Cardiovasc Surg, 48(3):323-331 (2007). "Evaluation of the topical hemostatic efficacy and safety of TISSEEL VH S/D fibrin sealant compared with currently licensed TISSEEL VH in patients undergoing cardiac surgery: a phase 3, randomized double-blind clinical study".
Lu et al., Biomacromolecules, 10:1032-1042 (2009). "Stabilization of Enzymes in Silk Films".
Lu et al., Acta Biomater. 6(4):1380-1387 (2010). "Water-Insoluble Silk Films with Silk I Structure".
Marcovich et al., Urology, 57:806-810 (2001). "Comparison of 2-Octyl Cyanoacrylate Adhesive, Fibrin Glue, and Suturing for Wound Closure in the Porcine Urinary Tract".
Megeed et al., Pharmaceutical Research, 19(7):954-959 (2002). "Controlled release of plasmid DNA from a genetically engineered silk-elastinlike hydrogel".
Nazarov et al., Biomacromolecules, 5:718-726 (2004). "Porous 3-D Scaffolds from Regenerated Silk Fibroin".
Pandit et al., Archives of Biochemistry and Biophysics, 149:259-268 (1972). "Studies on Silk Fibroin. I. Molecular Weight, Sedimentation Coefficient, Viscosity and Optical Rotation of Silk Fibroin from Carbonate-Extracted Silk Fiber".
Petrini et al., Journal of Materials Science: Materials in Medicine, 12:849-853 (2001). "Silk fibroin-polyurethane scaffolds for tissue engineering".
Preul et al., J Neurosurg, 107:642-650 (2007). "Application of a hydrogel sealant improves watertight closures of duraplasty onlay grafts in a canine craniotomy model".
Pritchard et al., Macromol. Biosci., 13:311-320 (2013). "Effect of Silk Protein Processing on Drug Delivery from Silk Films".
Rajkhowa et al., Journal of Applied Polymer Science, 119:1339-1347 (2011). "Molecular Weight and Secondary Structure Change in Eri Silk During Alkali Degumming and Powdering".
Reneker et al., Nanotechnology, 7:216-223 (1996). "Nanometre diameter fibres of polymer, produced by electrospinning".
Samal et al., Macromol. Mater. Eng., DOI: 10.1002/mame. 201200377 (2013). "Ultrasound Sonication Effects on Silk Fibroin Protein".
Sawyer et al., JAMA, 191(9):740-742 (1965). "Dextran therapy in thrombophlebitis" Abstract.
Silva et al., Macromol. Biosci., 8:000-000 (2008). "Genipin-Modified Silk Fibroin Nanometric Nets".
Soffer et al., J Biomater Sci Polym Ed., 19(5):653-664 Author Manuscript (2008). "Silk-Based Electrospun Tubular Scaffolds for Tissue Engineered Vascular Grafts".
Sofia et al., Journal of Biomedical Materials Research, 54(1):139-148 (2001). "Functionalized silk-based biomaterials for bone formation".
Spotnitz et al., Transfusion, 48:1502-1516 (2008). "Hemostats, sealants, and adhesives: components of the surgical toolbox".
Torchiana, J Card Surg, 18:504-506 (2003). "Polyethylene Glycol Based Synthetic Sealants: Potential Uses in Cardiac Surgery".
Tsukada et al., J. of Applied Polymer Science, 54(4):507-514 (1994). "Preparation and Application of Porous Silk Fibroin Materials".
U.S. Appl. No. 60/906,509, filed Mar. 13, 2007 by Omenetto et al.
U.S. Appl. No. 61/224,618, filed Jul. 10, 2009 by Numata et al.
Vanderhooft et al., Biomacromolecules, 8:2883-2889 (2007). "Synthesis and Characterization of Novel Thiol-Reactive Poly(ethylene glycol) Cross-Linkers for Extracellular-Matrix-Mimetic Biomaterials".
Wallace et al., J Biomed Mater Res (Appl Biomater), 58:545-555 (2001). "A Tissue Sealant Based on Reactive Multifunctional Polyethylene Glycol".
Wang et al., Langmuir, 21:11335-11341 (2005). "Biomaterial coatings by stepwise deposition of silk fibroin".
Wang et al., J Control Release, 134(2):81-90 (2009). "Growth Factor Gradients via Microsphere Delivery in Biopolymer Scaffolds for Osteochondral Tissue Engineering".
Wenk et al., Diss. Eth No. 18659 (2009). "Silk Fibroin As a Vehicle for Drug Delivery in Tissue Regeneration".
Wheat et al., Urol Clin North Am., 36(2):265-275 (2009). "Advances in Bioadhesives, Tissue Sealants, and Hemostatic Agents".
Wilson et al., PNAS, 98(24):13660-13664 (2001). "Surface organization and nanopatterning of collagen by dip-pen nanolithography".
Wray et al., J Biomed Mater Res Part B, 99B:89-101 (2011). "Effect of Processing on silk based biomaterials: Reproducibility and biocompatibility".
Yamada et al., Materials Science and Engineering C, 14:41-46 (2001). "Preparation of undegraded native molecular fibroin solution from silkworm cocoons".
Yamada et al., Thin Solid Films, 440:208-216 (2003). "AFM observation of silk fibroin on mica substrates: morphologies reflecting the secondary structures".
Yucel et al., J. Struct Biol., 170(2):406-412 (2010). "Non-equilibrium Silk Fibroin Adhesives".
Zhou et al., Proteins: Structure, Function, and Genetics, 44:119-122 (2001). "Silk Fibroin: Structural Implications of a Remarkable Amino Acid Sequence".
Zhou et al., Chem Commun, 2518-2519 (2001). "Preparation of a novel core-shell nanostructured gold colloid-silk fibroin bioconjugate by the protein in situ redox technique at room temperature".
Boison, D., "Adenosine kinase, epilepsy and stroke: mechanisms and therapies," TRENDS in Pharmacological Sciences, vol. 27, No. 12, pp. 652-658. 2006.
Fini, M., et al., "The healing of confined critical size cancellous defects in the presence of silk fibroin hydrogel," Biomaterials, 26 2005, pp. 3527-3536.
Giraud-Guille, M., et al., "Optimization of Collagen Liquid Crystalline Assemblies: Influence of Sonic Fragmentation," Journal of Structural Biology 113, 1994, pp. 99-106.
Hung, C. T., et al., "A Paradigm for Functional Tissue Engineering of Articular Cartilage via Applied Physiologic Deformational Loading," Annals of Biomedical Engineering, vol. 32, No. 1, 2004, pp. 35-49.
Isozaki, K., et al., "Ultrasound-Induced Gelation of Organic Fluids with Metalated Peptides," Angewandte Chem., 2007, pp. 2913-2915.
Kemmere, M. F., et al., "A Novel Process for Ultrasound-Induced Radical Polymerization in $CO_2$-Expanded Fluids," Macromolecular Materials and Engineering, 2005, pp. 302-310.
Kim, U., et al., "Structure and Properties of Silk Hydrogels," Biomacromolecules, 2004, 5, pp. 786-792.

(56) References Cited

OTHER PUBLICATIONS

Kim, U., et al., "Three-dimensional aqueous-derived biomaterial scaffolds from silk fibroin," Biomaterials, 26, 2005, pp. 2775-2785.

Lee, C. H., et al., "Biomedical applications of collagen," International Journal of Pharmaceutics, 221, 2001, pp. 1-22.

Lewus, K. E., et al., "In Vitro Characterization of a Bone Marrow Stem Cell-Seeded Collagen Gel Composite for Soft Tissue Grafts: Effects of Fiber Number and Serum Concentration," Tissue Engineering, vol. 11, No. 718, 2005, pp. 1015-1022.

Majumdar, M. K., et al., "Isolation, Characterization, and Chondrogenic Potential of Human Bone Marrow-Derived Multipotential Stromal Cells," Journal of Cellular Physiology, 185, 2000, pp. 98-106.

Matsumoto, A., et al., "Mechanisms of Silk Fibroin Sol—Gel Transitions," J. Phys. Chem, B, 2006, 110, pp. 21630-21638.

Mauck, R. L., et al., "Chondrogenic differentiation and functional maturation of bovine mesenchymal stem cells in long-term agarose culture," OsteoArthritis and Cartilage, 2006, 14, pp. 179-189.

Meinel, L., et al., "Engineering bone-like tissue in vitro using human bone marrow stem cells and silk scaffolds," J. Biomed. Mater. Res. A, 2004, pp. 25-34.

Meinel, L., et al., "Engineering Cartilage-Like Tissue Using Human Mesenchymal Stem Cells and Silk Protein Scaffolds," Biotechnol. Bioeng., 88, 2004, pp. 379-391.

Motta, A., et al., "Fibroin hydrogels for biomedical applications: preparation, characterization and in vitro cell culture studies," J. Biomater. Sci. Polymer Edn, vol. 15, No. 7, 2004, pp. 851-864.

Nuttelman, C. R., et al., "Synthetic hydrogel niches that promote hMSC viability," Matrix Biology 24, 2005, pp. 208-218.

Nuttelman, C. R., et al., "The effect of ethylene glycol methacrylate phosphate in PEG hydrogels on mineralization and viability of encapsulated hMSCs," Biomaterials 27, 2006, pp. 1377-1386.

Paulusse, J.M.J., et al., "Ultrasound in Polymer Chemistry: Revival of an Established Technique," J. Polym. Sci. Part A: Polym. Chem. 44, 2006, pp. 5445-5453.

Ramdi, H., et al., "Influence of Matricial Molecules on Growth and Differentiaion of Entrapped Chondrocytes," Experimental Cell Research 207, 1993, pp. 449-454.

Seida, Y., et al., "Phase Behavior of N-Isopropylacrylamide/Acrylic Acid Copolymer Hydrogels Prepared with Ultrasound," Journal of Applied Polymer Science, vol. 90, 2003, pp. 2449-2452.

Smidsrød, O., et al., "Alginate as immobilization matrix for cells," Trends Biotech, 1990, pp. 71-78.

Stathopulos, P. B., et al., "Sonication of proteins causes formation of aggregates that resemble amyloid," Protein Science, 2004, pp. 3017-3027.

Yokoi, H., et al., "Dynamic reassembly of peptide RADA16 nanofiber scaffold," Proc. Nat. Acad. Sci. USA, 2005, pp. 8414-8419.

\* cited by examiner

METHOD FOR SILK FIBROIN GELATION USING SONICATION

RELATED APPLICATIONS

This application is a continuation under 35 U.S.C. 120, 121, or 365(c) of U.S. patent application Ser. No. 12/601,845 filed Jan. 12, 2010 which is a 35 U.S.C. §371 National Stage Entry of International Application No. PCT/US2008/065076 filed on May 29, 2008, which designates the United States, and which claims the benefit of priority under 35 U.S.C. §119(e) of U.S. Provisional Application No. 60/940,554, filed May 29, 2007. The contents of each of these applications is hereby incorporated by reference in its entirety.

This invention was made with U.S. government support under Tissue Engineering Research Center Grant No. P41 EB002520 awarded by the National Institutes of Health. The government has certain rights in the invention.

FIELD OF THE INVENTION

This invention provides for methods of rapidly forming silk fibroin gelation through ultrasonication. The hydrogels formed from the method are useful, for example, as biodelivery vehicles.

BACKGROUND

Biocompatible and biodegradable polymer hydrogels are useful carriers to deliver bioactive molecules and cells for biomedical applications, such as in tissue engineering and controlled drug release. Purified native silk fibroin forms β-sheet-rich crosslinked hydrogel structures from aqueous solution, with the details of the process and gel properties influenced by environmental parameters. Previous gelation times often took days to weeks for aqueous native silk protein solutions, with high temperature and low pH responsible for increasing gelation kinetics. Those conditions, although suitable for incorporation of some bioactive molecules, may be too slow for incorporation of active cell and labile bioactive molecules.

Thus, there is a need in the art for a process of rapidly forming silk fibroin gelation at mild physiological conditions.

SUMMARY OF THE INVENTION

This invention relates to a process of rapidly forming silk fibroin gelation. The process exposes silk fibroin to a treatment comprising ultrasonication for a sufficient period of time to initiate gelation. For example, under particular conditions the gelation occurs within 24 hours of the ultrasonication treatment.

An embodiment of the invention also relates to a method of controlling gelation time of silk fibroin by contacting a silk fibroin solution with an ultrasonication treatment for a sufficient period of time to initiate gelation. In one example the gelation time is under two hours.

Another embodiment relates to a method of encapsulating an agent in silk fibroin. The method comprises exposing a silk fibroin solution to an ultrasonication treatment for a period of time to initiate gelation, and introducing the agent to the silk fibroin solution before substantial gelation occurs in the silk fibroin solution, thereby forming a silk-fibroin-encapsulated agent. Alternatively, the agent may be added to the silk fibroin before sonication. The agent can be a therapeutic agent, such as a drug, or a biological material, such as a cell. For example, human bone marrow derived mesenchymal stem cells (hM-SCs) were successfully incorporated into silk fibroin hydrogels after sonication, followed by rapid gelation and sustained cell function.

The hydrogels resulting from the methods of the invention exhibit both good mechanical properties and proteolytic degradation profiles. For example, sonicated silk fibroin solutions at 4%, 8%, and 12% (w/v), followed by adding hMSCs, gelled within 0.5 hours to 2 hours. The cells grew and proliferated in the 4% gels over twenty-one days. Additionally, low concentrations of $K^+$ and low pH may be used to promote gelation.

DESCRIPTION OF THE DRAWINGS

FIG. 2A shows Circular Dichroism (CD) measurements on sonicated 2% (w/v) silk fibroin aqueous solutions with wavelength scans taken every 8 min after sonication for 120 min. FIG. 2B shows a chart of ellipticity increase at 217 nm (β-sheet structure peak) recorded against time. FIG. 2C is a schematic illustration of mechanism of silk gelation. The gelation process contains two kinetic steps (a) structural change from random coil to β-sheet with some inter-chain physical cross-links occurring in a short time frame; (b) β-sheet structure extended, large quantity of inter-chain β-sheet cross-links formed, and molecules organized to gel network over a relatively long time frame.

FIG. 3C shows the effects of adjusting the pH of the silk fibroin aqueous solution prior to sonication. Sonication was performed at 20% amplitude for 15 sec for all samples. Values are average±standard deviation of a minimum of N=3 samples for each group. *, ◊ Significant differences between the groups (Student's t-test, $p<0.05$).

DETAILED DESCRIPTION

Figure 1:
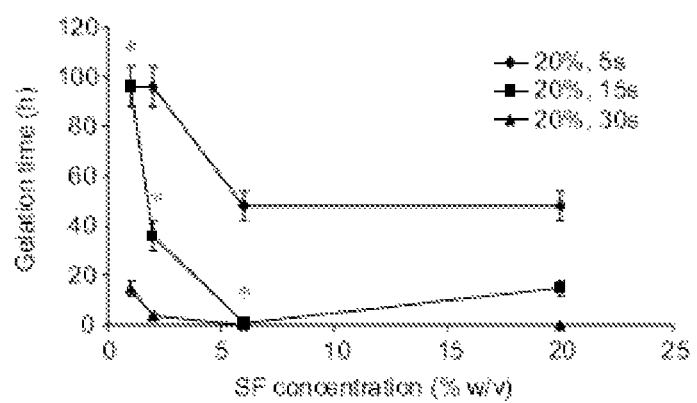
FIG. 1 depicts silk fibroin (SF) gelation under various sonication conditions. 0.5 ml of aqueous solution was used, sonication was performed at 20% amplitude and time varied from 5 sec to 30 sec. Values are average±standard deviation of a minimum of N=3 samples for each group. *Significant differences between the groups (Student's t-test, $p<0.01$).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

This invention relates to a process of rapidly forming silk fibroin gelation. The process exposes silk fibroin to a treatment comprising ultrasonication for a sufficient period of time to initiate gelation. This approach provides for ultrasonication-based methods used to accelerate the sol-gel transition in a temporally controllable manner. Gelation time can be controlled from minutes to hours based on the sonication parameters used (energy output, duration time, and others) and silk fibroin concentration within physiologically relevant conditions. After sonication, the silk fibroin undergoes a rapid structural change from random coil to β-sheet, corresponding to gelation. An agent can be added, for example a therapeutic agent or a biological agent, either before, during or after the sonication treatment, and encapsulated upon gelation. The present invention thus provides for methods useful for various biomedical applications, such as those in which the encapsulation of cells is time sensitive.

Hydrogels are considered useful scaffolds for encapsulation and delivery of cells and bioactive molecules, such as for tissue engineering and cell therapeutic applications, due to their high water content; usually >30% (Park & Lakes, BIOMATS: INTRO. (2nd ed., Plenum Press, NY, 1992). Hydrogels used in these types of applications have mechanical and structural properties similar to some tissues and extracellular matrices (ECM), therefore, they can be implanted for tissue restoration or local release of therapeutic factors. To encapsulate and deliver cells, hydrogels should, preferably, be formed without damaging cells, be nontoxic to the cells and the surrounding tissue, be biocompatible, have suitable mass transport capability to allow diffusion of nutrients and metabolites, have sufficient mechanical integrity and strength to withstand manipulations associated with implantation, have controllable lifetimes, and should maintain gel volume after implantation for a reasonable period of time depending on the application (Drury & Mooney, 24 Biomats. 4337-51 (2003).

A variety of synthetic materials, such as poly(ethylene oxide) (PEO), poly(vinyl alcohol) (PVA), poly(acrylic acid) (PAA), polypropylene furmarate-co-ethylene glycol) (P(PF-co-EG)), and naturally derived materials, such as agarose, alginate, chitosan, collagen, fibrin, gelatin, and hyaluronic acid (HA) have been used to form hydrogels. Gelation occurs when the polymer chains crosslink either chemically or physically into networks, triggered by chemical reagents (e.g., cross-linkers) or physical stimulants (e.g., pH and/or temperature). Hydrogels formed from synthetic polymers offer the benefit of gelation and gel properties that are controllable and reproducible, through the use of specific molecular weights, block structures, and crosslinking modes. Generally, gelation of naturally derived polymers is less controllable, although they tend to be useful as carriers of cell and bioactive molecules for tissue engineering and implantable medical devices because their macromolecular properties are more closely aligned to the extracellular matrix and the degradation products are nontoxic (Lee et al., 221 Int'l J. Pharma. 1-22 (2001); Smidsrød et al., 8 Trends Biotech. 71-78 (1990).

Among naturally derived biomaterials, silk fibroin protein, the self-assembling structural protein in natural silkworm fibers, has been studied because of its excellent mechanical properties, biocompatibility, controllable degradation rates, and inducible formation of crystalline β-sheet structure networks (Altman et al., 24 Biomats. 401-16 (2003); Jin & Kaplan, 424 Nature 1057-61 (2003); Horan et al., 26 Biomats. 3385-93 (2005); Kim et al., 26 Biomats. 2775-85 (2005); Ishida et al., 23 Macromolecules 88-94 (1990); Nazarov et al., 5 Biomacromolecules 718-26 (2004)). Silk fibroin has been fabricated into various material formats including films, three dimensional porous scaffolds, electrospun fibers and microspheres for both tissue engineering and controlled drug release applications (Jin et al., 5 Biomacromolecules 711-7 (2004); Jin et al., 3 Biomacro-molecules, 1233-39 (2002); Hino et al., 266 J. Colloid Interface Sci. 68-73 (2003); Wang et al., 117 J. Control Release, 360-70 (2007)). See also U.S. patent application Ser. No. 11/020,650; Ser. No. 10/541,182; Ser. No. 11/407,373; and Ser. No. 11/664,234; PCT/US07/020789; PCT/US08/55072.

In nature, silk fibroin aqueous solution is produced in the posterior section of silkworm gland and then stored in the middle section at a concentration up to 30% (w/v) and contains a high content of random coil or alpha helical structure. During fiber spinning into air, high shear force and elongational flow induces self-assembly and a structural transition to the β-sheet structure, leading to the formation of solid fibers (Vollrath & Knight, 410 Nature, 541-48 (2001)). The presence of metallic ions and pH changes in different sections of the gland influence this transition (Chen et al., 3 Biomacromolecules 644-8 (2002); Zhou et al., 109 J. Phys. Chem. B 16937-45 (2005); Dicko et al., 5 Biomacromolecules 704-10 (2004); Terry et al., 5 Biomacromolecules 768-72(2004)). In vitro, purified silk fibroin aqueous solutions undergo self-assembly into β-sheet structures and form hydrogels. This sol-gel transition is influenced by temperature, pH, and ionic strength (Wang et al., 36 Int'l J. Biol. Macromol. 66-70 (2005); Kim et al., 5 Biomacromolecules 786-92 (2004); Matsumoto et al., 110 J. Phys. Chem. B 21630-38 (2006)).

The compressive strength and modulus of silk hydrogels increases with an increase in silk fibroin concentration and temperature (Kim et al., 2004).

Silk fibroin hydrogels are of interest for many biomedical applications. For example, fibroin hydrogels were used as a bone-filling biomaterial to heal critical-size cancellous defects of rabbit distal femurs, where the silk gels showed better bone healing than the poly(D,L lactide-glycolide) control material (Fini et al., 26 Biomats. 3527-36 (2005)).

For many cell-based applications, gelation must be induced under mild conditions in a relatively short period of time (within hours). Silk gelation time may be prohibitively long, however, unless nonphysiological treatments are considered (such as low pH, high temperature, additives) in the absence of chemical modifications to the native silk fibroin protein. For silk fibroin concentrations from 0.6% to 15% (w/v), days to weeks were required for the sol-gel transition at room temperature or 37° C. (Kim et al., 2004; Matsumoto et al., 2006; Fini et al., 2005)). Adding salts at concentrations above physiological levels does not significantly alter the gelation kinetics (Kim et al., 2004). Lowering pH (pH<5) or increasing temperature (>60° C.) could reduce the gelation time to a few hours (Kim et al., 2004; Fini et al., 2005; Motta et al., 15 J. Biomater. Sci. Polymer. Edu. 851-64 (2004)), but these conditions could potentially alter cell function and affect cell viability.

In the present invention, novel methods to accelerate the process and control silk fibroin gelation are accomplished through ultrasonication. More specifically, a new ultrasonication-based method is presented that accelerates the sol-gel transition in a temporally controllable manner. Mechanistically, the process induces physical β-sheet crosslinking via alteration in hydrophobic hydration of the fibroin protein chains. This permits cell additions post-sonication, followed by rapid gelation. Gelation time may be controlled from minutes to hours based on the sonication parameters used (energy output and duration time) and silk fibroin concentrations. The method further provides for manipulation of the pH and salt concentration effects on gelation; the dynamic silk structural changes after gelation; and the behavior of encapsulated cells, such as human bone marrow derived mesenchymal stem cells (hMSCs) in silk gels.

Any type of silk fibroin may be used according to the present invention. Silk fibroin produced by silkworms, such as *Bombyx mori*, is the most common and represents an earth-friendly, renewable resource. Organic silkworm cocoons are commercially available. There are many different silks, however, including spider silk, transgenic silks, genetically engineered silks, and variants thereof, that may be used alternatively. An aqueous silk fibroin solution may be prepared from the silkworm cocoons using techniques known in the art. Suitable processes for preparing silk fibroin solution are disclosed in, for example, U.S. patent application Ser. No. 11/247,358; WO/2005/012606; and PCT/US07/83605. For instance, silk used in a silk biopolymer may be attained by extracting sericin from the cocoons of *B. mori*.

Substantial gelation usually occurs within twenty-four hours after the ultrasonication treatment. For example, the silk fibroin gel forms less than four hours after ultrasonication treatment, such as within two hours after the ultrasonication treatment. In a particular embodiment, the silk fibroin undergoes gelation at a time period ranging from about five minutes to about two hours after the ultrasonication treatment. Thus, depending on requirements, gelation time can occur from minutes to hours, based on the ultrasonication treatment used in the preparation of the solution.

Ultrasonication treatments are known in the art. For the purposes of this application, the terms "ultrasonication" and "sonication" are being used interchangeably and carry the same meaning Ultrasonication treatments may be performed in any manner known in the art that applies ultrasonication to the silk fibroin. The ultrasonication treatment may involve exposing the silk fibroin to sonication one time, or may involve multiple separate exposures. Sonication has been studied in the context of protein structural changes (Meinel et al., 71 J. Biomed. Mater. Res. A 25-34 (2004); Meinel et al., 88 Biotechnol. Bioeng. 379-91 (2004)) and has been used to generate large liquid-gas interfaces, local heating effects, mechanical/shear stresses, and free radical reactions. In contrast, in other studies relating to peptide gelation, the assembled peptide nanofibers in the gel were disrupted into smaller fragments by sonication (Hung et al., 32 Ann. Biomed. Eng. 35-49 (2004)). In the context of polymer sol-gel transitions, sonication has typically been used to break down gel networks and reliquify hydrogels. The present invention provides for the novel use of sonication to induce silk sol-gel transition.

The ultrasonication treatment should last for a period of time sufficient to initiate the gelation process, but not so long as to compromise the mechanical properties of the hydrogel. Typically, ultrasonication treatments may last from about 5 seconds to about 60 seconds, depending on the amount of silk fibroin used, the concentration of the solution, and other factors appreciated by those of ordinary skill in the art. For example, the ultrasonication treatments last from about 15 seconds to about 45 seconds. Gelation typically begins at the onset of the ultrasonication treatment and continues after the treatment ends.

The ultrasonication treatment may include other treatments to assist in the gelation process. For example, the treatment may include a salt solution. Salt solutions are known in the art to assist in inducing gelation. Typical salt solutions containing ions of potassium, calcium, sodium, magnesium, copper, and/or zinc may be used. Potassium may be advantageous in a salt solution in this context.

The treatment can also include adjusting the pH of the aqueous fibroin solution. As known in the art, adjusting the pH of the aqueous solution can assist in inducing gelation. In particular, adjusting the pH either higher or lower can be effective. Thus, for example, an aqueous solution having a pH of about pH 4 or lower, or about pH 7.5 or higher, may be used.

In particular, using a potassium salt solution at low concentrations and at a low pH is often effective. A particular embodiment is directed towards the use of a potassium salt where the salt concentration is less than 100 mM and the pH of the solution is about pH 4 or lower.

The invention also provides for a method of controlling gelation time of silk fibroin by contacting a silk fibroin solution with an ultrasonication treatment for a sufficient period of time to initiate gelation under conditions that gelation occurs within about two hours. The sonication process results in interactions among the silk fibroin chains. A particular embodiment provides for a method of controlling gelation time so that the silk fibroin undergoes gelation at a time period ranging from about five minutes to about two hours after the ultrasonication treatment.

Additionally, various other factors can be used to control the gelation time. For example, the gelation time can be controlled through the amplitude of the ultrasonication and the concentration of the silk fibroin solution. For example, the amplitude ranges from about 25% to about 35% power output (typically, 7 watts to 10 watts) and the concentration of the silk fibroin ranges from about 10% to about 15% (w/v). In another embodiment, the amplitude ranges from about 25% to about 55% power output (typically, 7 watts to 21 watts) and the concentration of the silk fibroin ranges from about 5% to about 10% (w/v). Those of ordinary skill in the art, in light of the present application, are able to alter the amplitude of the ultrasonication and the concentration of the silk fibroin solution to produce the desired level of gelation and the desired time frame in which gelation occurs.

The gelation time may also be controlled by adding a salt solution and adjusting the concentration of the silk fibroin solution and the concentration of the salt solution. The salt solution may include potassium ions, but other salt solutions may be used. In a specific embodiment, the concentration of the silk fibroin is 4% (w/v) or lower, and the concentration of the potassium salt solution ranges from 20 mM to 100 mM.

Additionally, gelation time may be controlled by adjusting the concentration and pH of the salt solution, especially when the salt solution contains potassium ions. In a particular embodiment, the salt solution is a potassium salt solution at a pH of about pH 4 or lower. For example, the potassium salt solution has a concentration of 20 mM to 100 mM.

The invention also relates to a method of encapsulating at least one agent in silk fibroin. The method comprises (a) exposing a silk fibroin solution with an ultrasonication treatment for a period of time to initiate gelation; and (b) introducing the agent into the silk fibroin before substantial gelation occurs in the silk fibroin, thus forming a silk-fibroin encapsulated agent. The agent may be introduced into the silk fibroin solution before, during, or after the ultrasonication treatment.

The agent can represent any material capable of being encapsulated in the silk fibroin gel. For example, the agent may be a therapeutic agent, such as small molecules and drugs, or a biological material, such as cells (including stem cells), proteins, peptides, nucleic acids (DNA, RNA, siRNA), PNA, aptamers, antibodies, hormones, growth factors, cytokines, or enzymes. Encapsulating either a therapeutic agent or biological material is desirous because the encapsulated product can be used for biomedical purposes.

If a therapeutic agent is being encapsulated, the therapeutic agent can be introduced into the silk fibroin solution before, during, or after the ultrasonication treatment, as most therapeutic agents are not affected adversely by sonication. On the other hand, if a biological material is being encapsulated, the biological material may be affected adversely by the sonication and should typically not be introduced into the silk fibroin solution until after the ultrasonication treatment. This may not be necessary for all biological material, but sonication has been known to damage or destroy living cells, so caution may be applied.

When an agent is introduced after the ultrasonication treatment, the conditions of the ultrasonication treatment may be adjusted so that gelation occurs some period of time after the ultrasonication treatment. If gelation occurs during the ultrasonication treatment or immediately thereafter, an insufficient amount of time may exist to introduce the agent into the silk fibroin solution. For example, when the agent is introduced after the ultrasonication treatment, the silk fibroin undergoes gelation at a time period ranging from about five minutes to about two hours after the ultrasonication treatment.

If an agent is introduced before or during the ultrasonication treatment, gelation can occur during the ultrasonication treatment, immediately thereafter, or a period of time after the ultrasonication treatment. Therefore when the agent is introduced before or during the ultrasonication treatment, the silk fibroin may undergo gelation within about two hours after the ultrasonication treatment.

When introducing therapeutic agents or biological material into the silk fibroin, other materials known in the art may also be added with the agent. For instance, it may be desirable to add materials to promote the growth of the agent (for biological materials), promote the functionality of the agent after it is released from the encapsulation, or increase the agent's ability to survive or retain its efficacy during the encapsulation period. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Additional options for delivery via the gels include DNA, siRNA, antisense, plasmids, liposomes and related systems for delivery of genetic materials; peptides and proteins to active cellular signaling cascades; peptides and proteins to promote mineralization or related events from cells; adhesion peptides and proteins to improve gel-tissue interfaces; antimicrobial peptides; and proteins and related compounds.

The silk-fibroin encapsulated therapeutic agents or biological material are suitable for a biodelivery device. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US207/020789; PCT/US08/55072.

The silk fibroin hydrogel structure enables the biodelivery vehicle to have a controlled release. Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases.

Further regarding the approach to inducing silk gel formation using sonication, samples of 0.5 mL silk fibroin aqueous solutions at concentrations of 1%, 2%, 6%, and 20% (w/v) were sonicated as described below. When power output was kept constant (20% amplitude), silk fibroin gelation time decreased with increased sonication time (FIG. 1). For every increase in silk concentration from 1% to 6% (w/v), the gelation time decreased significantly ($p<0.01$ between * samples in FIG. 1). The 20% (w/v) sample had a similar or even longer gelation time than the 6% (w/v) sample (FIG. 1). This outcome for the 20% sample is likely due to the high viscosity of the solution, thus sonication waves could not effectively propagate in the solution. When the power output above 30% amplitude was used, sonication generated thick foams and the silk fibroin did not gel in a homogeneous manner.

This foaming was not observed when the volume for sonication was increased to 5 ml, even at power levels as high as 55% amplitude. When higher concentrations were sonicated at volumes exceeding 5 ml, however, heterogeneous gelation occurred. Small volumes of silk solution (without autoclaving) were used for sonication optimization and gel characterizations (pH, salt effect, and CD measurement), and autoclaved silk solutions were used for mechanical, degradation, and cell encapsulation studies. Interestingly, when compared with the original solutions, autoclaving did not significantly change the sonication parameters used and the related gelation times, suggesting that silk fibroin protein retained important features of its original solution-state structure and capability of structural transition to β-sheet state in forming a gel after autoclave. Structural alterations due to autoclave treatments may be investigated further, but this aspect provides for ease in commercial-scale preparation of pharmaceutical products.

Figures 2A, 2B:
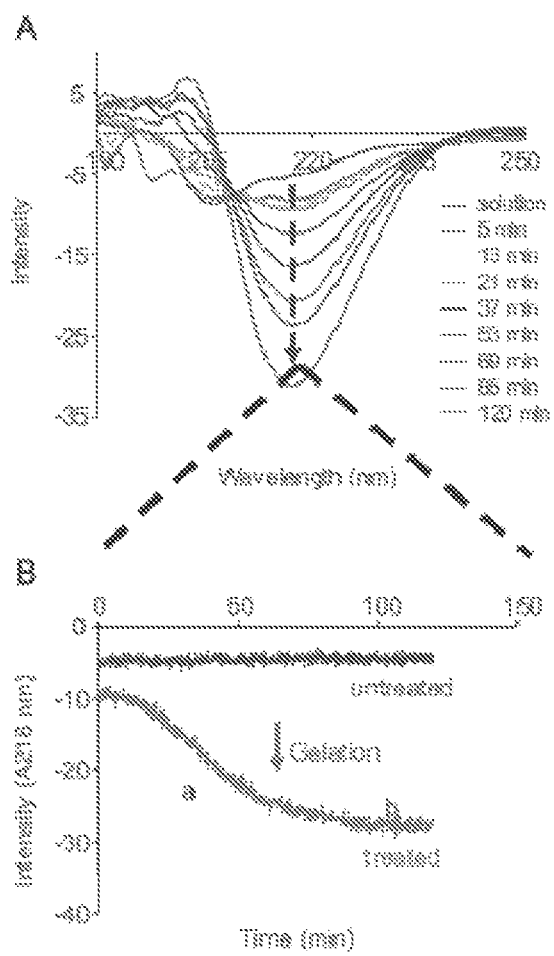
FIGS. 2A-2C depict the dynamic silk β-sheet structure formation during the gelation process.
Figure 2C:
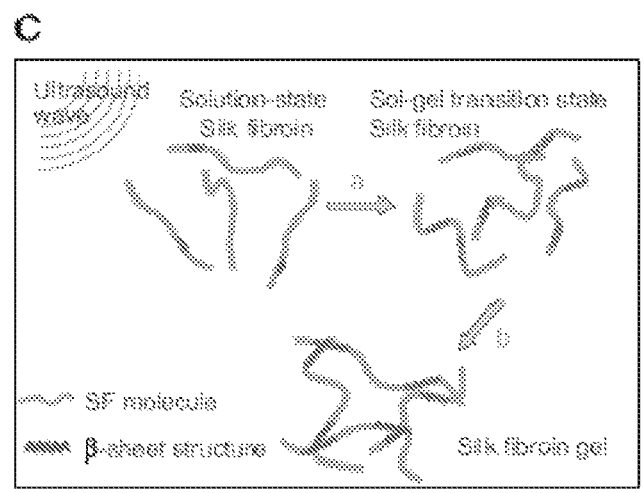

During gelation of silk fibroin, the sol-gel transition was linked to an increase in β-sheet formation by observed changes in CD measurements (FIG. 2A). After sonication, rapid formation of β-sheet structure was observed, followed by a slower transition, based on the increase of ellipticity at 217 nm (FIG. 2B). Silk fibroin gelation occurred at this transition point, where the initial rapid formation of β-sheet structure slowed. This transition is consistent with studies previously undertaken (Matsumoto et al., 2006), suggesting that similar mechanisms may be involved. The formation of β-sheet structure results from altered hydrophobic interaction and the subsequent physical cross-links. This initial step is followed by slower organization of the chains and formation of a gel network within a relatively long timeframe compared with the initial sonication-induced changes. This two-step silk gelation mechanism is schematically depicted in FIG. 2C.

The parameters studied to influence rates of gelation can be viewed as a method to recapitulate the natural silkworm spinning process. The key processing parameters include sonication effects, as a mimic for increased shear forces experienced at the anterior division of the silkworm gland, cation type and concentrations, and pH.

It is accepted that, in sonication, mechanical vibration causes the formation and collapse of bubbles. As a result of this cavitation, the media may experience extreme local effects: heating (10,000 K), high pressure (200 bar) and high strain rates ($10^7$ $s^{-1}$) (Paulusse & Sijbesma, 44 J. Polym. Sci.-Polym. Chem. 5445-53 (2006); Kemmere et al., 290 Macromol. Mater. Eng. 302-10 (2005). These physical phenomena have been exploited in a variety of applications, including self-assembly and gelation of N-isopropylacrylamide/acrylic acid copolymer (Seida et al., 90 J. Appl. Polym. Sci. 2449-52 (2003)), organic fluids with metalated peptides (Isozaki 119 Angew Chem. 2913-15 (2007)), and synthetic self-assembling peptides (Yokoi et al., 102 Proc Nat Acad Sci USA 8414-19 (2005)). Aside from peptides, proteins such as human serum albumin and myoglobin have been studied with sonication as an approach to characterize aggregation and self-assembly related to disease states (Stathopulos et al., 13 Protein Sci. 3017-27 (2004); Mason & Peters, PRACTICAL SONOCHEM: USES & APPL. ULTRASOUND (2nd ed., Chichester, West Sussex, UK (2002)).

Given the breadth of behavior of polymer systems in response to sonication, it is likely that several physical factors related to sonication, including local temperature increases, mechanical/shear forces, and increased air-liquid interfaces affect the process of rapid gelation of silk fibroin. In particular, sonication-induced changes in hydrophobic hydration would result in the accelerated formation of physical cross-links, such as initial chain interactions related to β-sheet formation. In the present study, during the sonication process, the solution temperature increased from room temperature to 40° C.-71° C. for the short period of time (5 min-6 min), which reflects a transient spike in local temperature. In a past study, gelation required a few days when bulk samples were maintained at 60° C., without sonication (Kim et al., 2004). Therefore, local temperature effects likely contribute toward the increased gelation kinetics, but are not solely responsible for the shortduration responses found. Localized chain dynamics and changes in hydration states of the hydrophobic chains, influenced by the transient temperature increase, are likely responsible for the formation of the hydrophobic physical cross-links.

The unique hydrophobic block sequence features in silk fibroin chains are particularly suitable for this type of technique due to the critical role of water in the control of intra- and inter-chain interactions (Jin et al., 2003). It might be useful to extend the technique to other biopolymer systems to determine the impact of chain chemistry on sonication controlled processes of chain assembly. Sonication related collagen degradation, as a method to fragment chains to facilitate studies of reassembly, have been reported (Giraud-Guille & Besseau, 113 J. Struct. Biol. 99-106 (1994)). It should be noted that in the present approach did not result in significant chain degradation due to the short duration sonication process used, based on SDS-PAGE analysis.

Figure 3A:
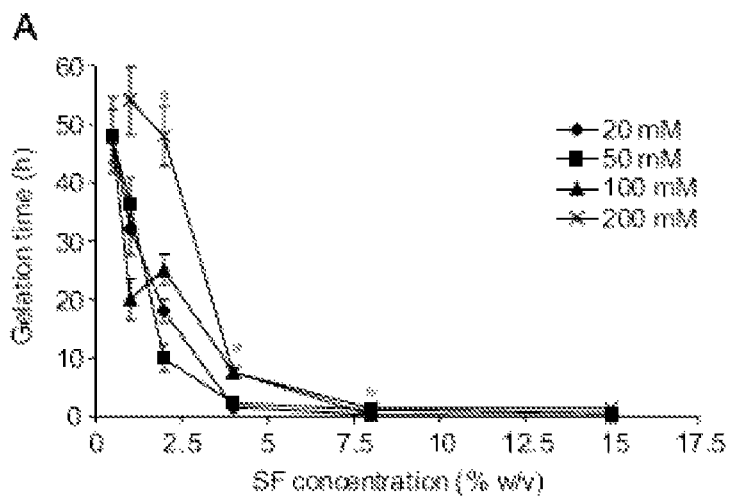
FIGS. 3A-3C show salt and pH effects on silk fibroin gelation. Prior to sonication, solutions at various concentrations were supplemented with $K^+$ (FIG. 3A) and $Ca^{2+}$ (FIG. 3B) to final concentrations of 20 mM-200 mM.
Figure 3B:
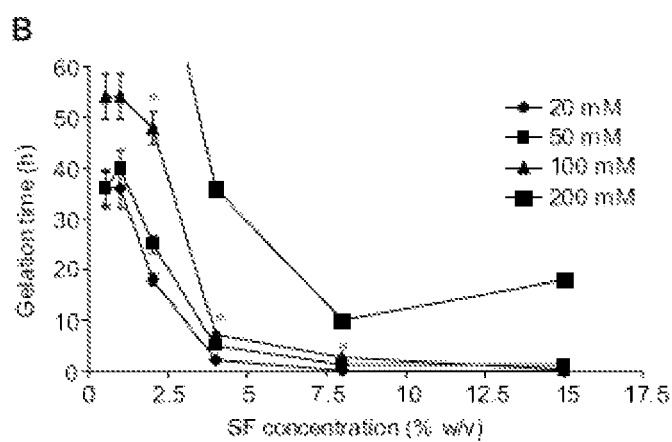

Silk fibroin aqueous solutions were supplemented with $K^+$ and $Ca^{2+}$ to various physiologically relevant concentrations prior to sonication. As shown in FIG. 3A, at low $K^+$ concentration (20 mM-50 mM), gelation time significantly decreased with increase in $K^+$ concentration (p<0.05 between * samples). At high $K^+$ concentration (100 mM-200 mM), however, gelation was inhibited (FIG. 3A). These outcomes were observed for silk fibroin concentrations ranging from 0.5% to 8% (w/v). Above 8%, no salt effect was observed as gelation occurred fast in all the samples (<2 min). Compared with $K^+$, $Ca^{2+}$ at the same concentrations induced slower silk fibroin gelation (compare FIGS. 3A and 3B). When $Ca^{2+}$ concentration was increased from 20 mM to 200 mM, silk fibroin gelation time significantly decreased (p<0.05 between * samples in FIG. 3B). In contrast, in previous work, $Ca^{2+}$ promoted silk fibroin gelation while $K^+$ had no effect (Kim et al., 2004), a different outcome than the observations in the present approach.

Figure 3C:
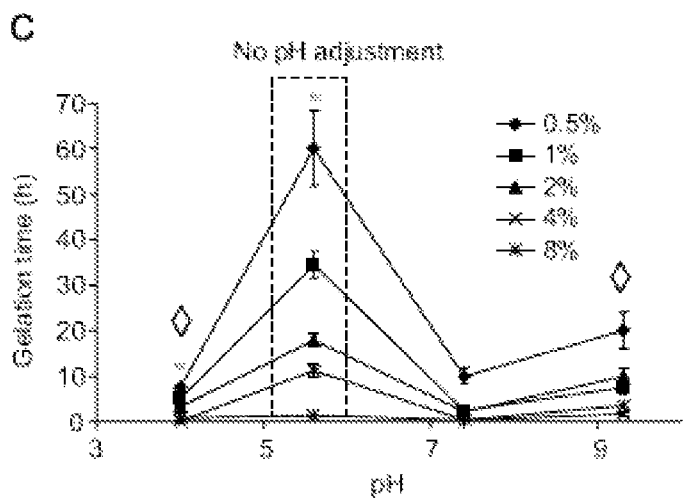

The pH of silk fibroin aqueous solution was adjusted prior to sonication in order to determine effects on gelation. Either decreasing or increasing pH promoted gelation (p<0.05 between * samples in FIG. 3C). The effect of lower pH (pH<4) was more pronounced than the higher pH (pH>9) in inducing gelation (p<0.05 between ◊ samples in FIG. 3C), consistent with previous studies (Kim et al, 2004; Matsumoto et al., 2006).

Figure 4A:
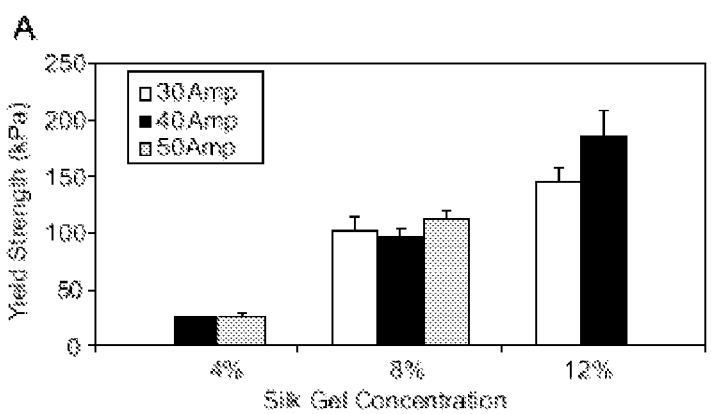
FIG. 4A-4C present charts analyzing the mechanical properties of silk fibroin hydrogels. The top two charts show published results from non-sonicated hydrogels, and the bottom two charts show sonication-processed hydrogels run in accordance with the invention. The two charts on the left show the effects of compressive strength, and the two charts on the right show the effects of compressive modulus. The hydrogels prepared from silk fibroin aqueous solutions (the two top charts) were run at various temperatures, the hydrogels that were sonicated (two bottom charts) were run at various sonication treatments. Values are average±standard derivation of a minimum of N=3 samples.
Figure 4B:
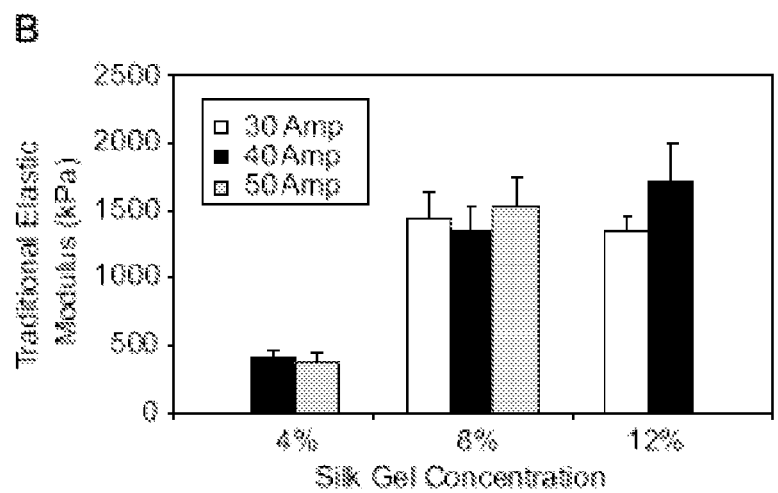
Figure 4C:
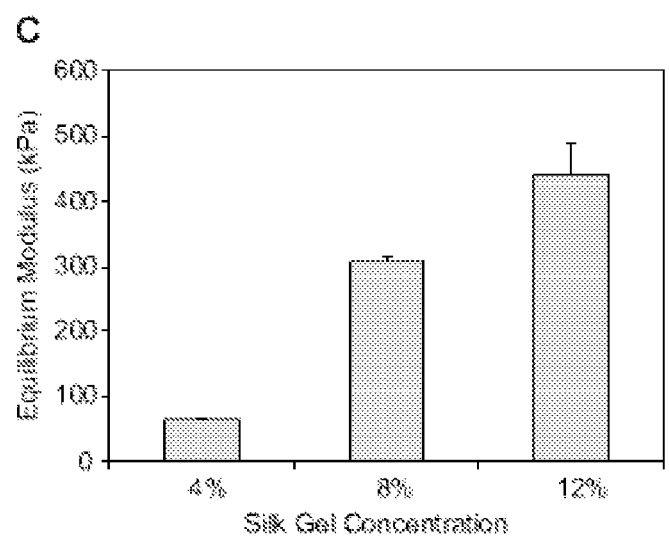

Stress/strain curves resulting from mechanical tests on the gels displayed linearity preceding a plateau region, suggesting that the gels have a large (~5%-10% strain) and likely viscoelastic characteristic, after which permanent damage is induced by crack formation. The gels fabricated in this study performed similarly to gels studied in previous work (Kim et al., 2004), in that the corresponding silk fibroin concentrations yielded similar values for both yield strength (FIG. 4A) and "traditional" elastic modulus (FIG. 4B). Both metrics appeared to be positively correlated with silk gel concentration. By inspection, the differences in silk fibroin concentration (w/v) were more significant determinants of final hydrogel mechanical properties, rather than variation due to sonication conditions (FIGS. 4A and 4B). Likewise, the equilibrium modulus values appeared to be positively correlated with silk gel concentration (FIG. 4C).

When compared with other degradable cell-encapsulating hydrogels, such as alginate, agarose, polyethylene glycol cross-linked gels, fibrinogen and other systems (Almany &

Seliktar 26(15) Biomats. 4023-29 (2005); Kong et al., 24(22) Biomats. 4023-29 (2003); Hung et al., 2004; Bryant et al., 86(7) Biotechnol Bioeng 747-55 (2004); Kang et al. 77(2) J. Biomed. Mater. Res. A 331-39 (2006); Rowley et al., 20(1) Biomats. 45-53 (1999); Broderick et al., 72 J. Biomed. Mater. Res. B-Appl Biomater. 37-42 (2004); Zhang et al., 15 J. Mater. Sci. Mater. Med. 865-75 (2004)), the high-concentration, rapidly forming silk hydrogels exhibited superior mechanical properties (Table 1). Data were collected based on similarities between cell-encapsulation and mechanical test protocols, in which either "traditional" or equilibrium modulus values were determined.

lagen and alginate, because of the potential of these cells for tissue repair or regeneration and long-term drug release (see Nuttelman et al., 24 Matrix Biol. 208-18 (2005); Nuttelman et al., 27 Biomats. 1377-86 (2006); Mauck et al., 14 Osteoarthr. Cartilage 179-89 (2006); Lewus & Nauman, 11 Tissue Eng. 1015-22 (2005); Majumdar et al., 185 J. Cell Physiol. 98-106 (2000); Boison, 27 Trends Pharmacol. Sci. 652-58 (2006)). Silk hydrogels with less than 4% (w/v) protein were difficult to manipulate due to physical limitations. Therefore, for hMSC encapsulation hydrogels of 4%, 8%, and 12% (w/v) silk fibroin were used. In all three gel concentrations, cells retained their original round shape and homogeneous distri-

TABLE 1

Comparative mechanical properties among gel systems from degradable polymers used for cell encapsulation

| Material | Traditional modulus (KPa) | Literature |
| --- | --- | --- |
| Silk Hydrogels | 369-1712 | Wang et al., 29 Biotmats. 1054-64 (2007) |
| Fibrinogen and Fibrinogen-PEG copolymer[a] | 0.02-4 | Almany & Seliktar, 2005 |
| Poly(1,8-octanediol citrate) (POC) | 10.4 | Kang et al., 2006 |
| PEG dimethacrylate-PLA copolymer, (photocross-linked) | 60-500 | Bryant et al., 2004 |
| Gelatin | 0.18 | Rowley et al., 1999 |
| Gelatin, glutaraldehyde cross-linked | 8.13 | Rowley et al., 1999 |
| Dex-AI/PNIPAAm | 5.4-27.7 | Zhang et al., 2004 |
| Alginate (calcium-cross-linked)[d] | ~25-125 | Smith & Mooney, 2003 |

| Material | Equilibrium modulus (KPa) | Literature |
| --- | --- | --- |
| Silk Hydrogels | 63-441 | Wang et al., 29 Biotmats. 1054-64 (2007) |
| Agarose (2% final concentration) | ~15 | Hung et al., 2004 |

[a] 5 mm dia × 5 mm height. Deformation rate of 1.5 mm/min, modulus based on average slope of the lower portion of stress-strain curve (<15%).
[b] 6 mm dia × 2.4 mm height. Deformation rate of 2 mm/min, modulus based on average slope of the initial portion of stress-strain curve.
[c] 5 mm dia × 1 mm height. Load-controlled deformation rate of 40-100 mN/min.
[d] 12.5 mm dia × 1.5 mm height. Load-controlled deformation rate of 25 mN/min, Young's modulus equivalent to the absolute value of the slope obtained between initial preload force 0.01N to 0.25N.
[e] 6 mm dia. Deformation rate of 0.5 mm/min, modulus based on average slope of the lower portion of stress-strain curve.
[f] 12.7 mm dia × 2 mm height. Deformation rate of 1 mm/min. Elastic moduli were obtained from the slope of the stress vs. strain curves, limited to the first 10% of strain.
[g] Equilibrium modulus calculated from the equilibrium stress and initial cross-sectional area at 10% strain.

Figure 5:
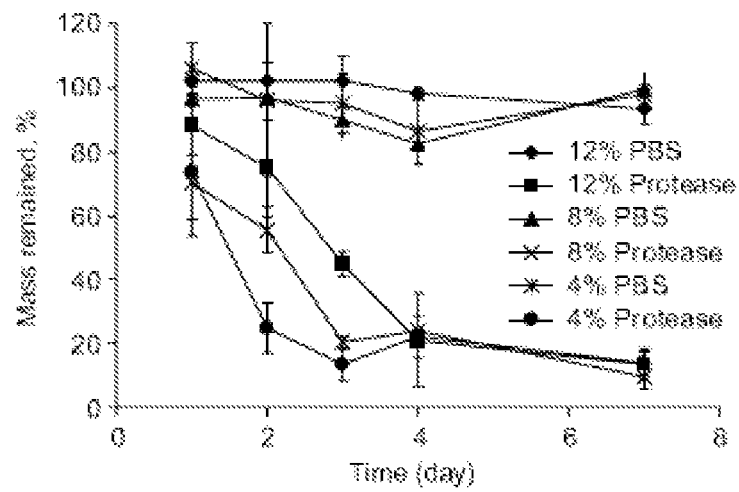
FIG. 5 depicts the enzymatic degradation of silk fibroin hydrogels. Hydrogels at 4%, 8%, and 12% (w/v) were prepared by sonication and immersed in either PBS, pH 7.4 (control) or protease XIV in PBS (5 U/ml) for seven days. The mass remaining was determined by comparing the wet weight of gel plugs at each time point with original wet weight. Values are average±standard derivation of a minimum of N=4 samples.

Enzymatic (protease XIV) degradation of silk fibroin films, porous solid scaffolds, and silk fibroin yarns have been studied previously (Horan et al., 2005; Kim et al., 2005; Jin et al., 2005). Using the same concentration of protease (5 U/mL), all silk fibroin hydrogels showed rapid degradation, with about 80% mass loss in the first four days, with a much slower rate of degradation afterwards (FIG. 5). The degradation of the hydrogels was silk fibroin concentration-dependent. When the concentration was increased from 4% to 12% (w/v), degradation time to reach 50% mass loss increased from 1.5 days to 3 days (FIG. 5). The control samples, silk fibroin hydrogels incubated in PBS instead of protease, were stable through the incubation period (FIG. 5). The fast degradation (within days) of silk hydrogels due to proteolytic processes may be suitable for some applications, such as in wound healing scenarios or rapid drug delivery. It should be noted, however, that the proteolytic degradation times discussed herein are in vitro; in contrast in vivo lifetimes are generally longer and the timeframes will be tissue-specific.

hMSCs have been successfully encapsulated in a variety of hydrogel systems, such as polyethylene glycol, agarose, colbution at day one. At day six, defects appeared on some cells in the 12% gel and cell morphology had changed. At day twenty-one, cells in the 4% gel were unchanged when compared with day one, while cells in the 8% and 12% gels were largely deformed and aggregated. Histological analysis revealed that hMSCs within the matrix of the 4% gel retained round-shape and were nonaggregated throughout the study, while those near the surface of the gels grew out of the gel and changed morphology from round-shape to spindle-like shapes from day six. All hMSCs, either spindle-like near the gel surface or round-shape encapsulated in the gel, were alive, as seen by green fluorescence in the live-dead assay. Therefore, hMSCs maintained their activity and function in the 4% silk hydrogel system for at least twenty-one days. hMSCs in the 8% and 12% gels, however, largely changed morphology and many of them died, aggregated and/or dissolved, as seen by the empty cavities in histological images and few green fluorescent spots in the live-dead assay. The control silk gel, with no cells encapsulated, showed a strong red fluorescence background, which masked the red fluorescence from dead cells in the live-dead assay.

Figure 6:
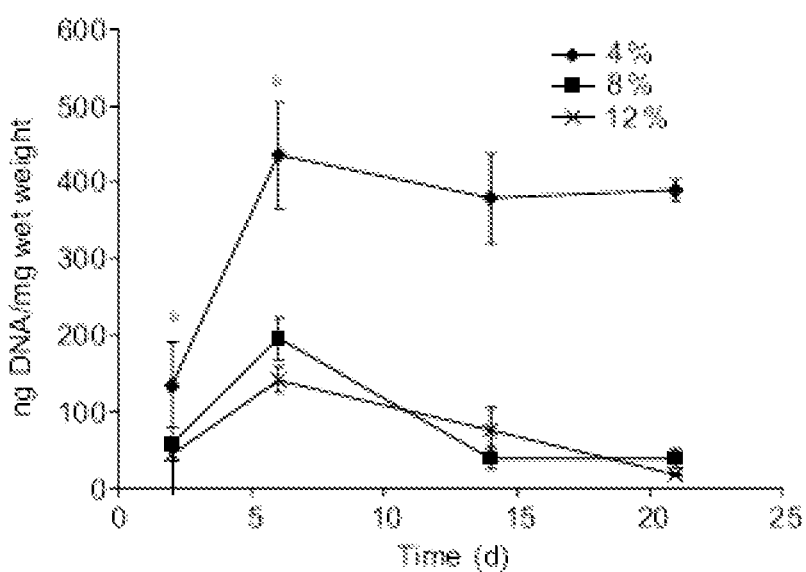
FIG. 6 depicts graphically DNA quantification of hMSCs encapsulated in silk fibroin hydrogels. DNA content in each gel group was analyzed with PicoGreen assay, and the results were normalized by the wet weight of each gel plug. Values are average±standard derivation of a minimum of N=4 samples. *Significant differences between the groups (Student's t-test, p<0.05).

These observations and conclusions were further supported by DNA quantification (PicoGreen assay) (FIG. 6). Cells significantly proliferated in all three hydrogels over the first 6 days (p<0.05 between * samples in FIG. 6). For the 4% gel, cell numbers stopped increasing after six days, indicating that maximal gel capacity for cell proliferation was reached. A similar phenomenon was observed in other hydrogel systems such as PEG and alginate (Nuttleman et al., 2006; Ramdi et al., 207 Exp. Cell Res. 449-54 (1993)). For the 8% and 12% gels, cell numbers decreased after six days, consistent with the microscopic, histological and live-dead observations. The loss of activity in the higher concentration gels is likely due to mass transport limitations, but also may be due to mechanical restrictions imposed at these higher gel concentrations. The possibility that silk gels were toxic to hMSCs can be excluded because the hMSCs growing on top of the silk gels at 4%, 8%, and 12% had growth rates similar to those growing on the control cell culture plate, and cell morphologies (spindle shape) were similar between all groups. Optimization of conditions to stabilize lower gel concentrations (1% and 2%) may be explored following the teachings provided herein, and the diffusion rates of oxygen and nutrients through various concentrations of silk gels may be studied in detail.

A novel method, based on ultrasonication, is provided herein, that allows the rapid formation of silk fibroin hydrogels. Gelation could be induced in minutes to hours, depending on the sonication power output and duration. Gelation was accompanied with β-sheet structure formation, due to changes in hydrophobic hydration. Low concentrations of $K^+$ and low pH accelerated gelation rates, whereas the presence of $Ca^{2+}$ and high concentrations of $K^+$ prevented gelation. The silk fibroin hydrogels had mechanical properties superior to those reported previously, in the range 369-1712 kPa based on compressive modulus. Gel mechanical strength increased with increased silk fibroin solution concentration. The 4% (w/v) silk fibroin hydrogels were suitable for encapsulation for hMSCs; the cells retained viability and proliferation in static culture conditions over weeks.

The invention will be further characterized by the following examples which are intended to be exemplary of the embodiments.

EXAMPLES

Example 1

Silk Fibroin Solutions

Silk fibroin aqueous stock solutions were prepared as previously described (Sofia et al., 54 J. Biomed. Mater. Res. 139-48 (2001)). Briefly, cocoons of *B. mori* were boiled for 40 min. in an aqueous solution of 0.02M sodium carbonate, and then rinsed thoroughly with pure water. After drying, the extracted silk fibroin was dissolved in 9.3M LiBr solution at 60° C. for 4 hours, yielding a 20% (w/v) solution. This solution was dialyzed against distilled water using Slide-a-Lyzer dialysis cassettes (MWCO 3,500, Pierce, Rockford, Ill.) for two days to remove the salt. The solution was optically clear after dialysis and was centrifuged to remove the small amounts of silk aggregates that formed during the process, usually from environment contaminants that are present on the cocoons. The final concentration of silk fibroin aqueous solution was approximately 8% (w/v). This concentration was determined by weighing the residual solid of a known volume of solution after drying. Silk solutions with lower concentrations were prepared by diluting the 8% solution with water. To obtain a silk solution with higher concentration, the 8% solution in a Slide-a-Lyzer dialysis cassettes (MWCO 3,500, Pierce) was dialyzed against 10% (w/v) PEG (10,000 g/mol) solution for at least 24 hours at room temperature (Jin & Kaplan, 2003; Kim et al., 2004). The volume was adjusted with water to reach the desired concentration. All solutions were stored at 4° C. before use.

Example 2

Silk Solutions with Various Salt Concentrations and pH

To determine the effect of salt concentration on silk gelation, KCl and $CaCl_2$ stock solutions at 1M were added to silk solutions to reach a final salt concentration of 20 mM to 200 mM. To determine the effect of pH on gelation, silk solutions were titrated with 1M HCl or NaOH solutions and the pH was monitored with a pH meter.

Example 3

Screening for Silk Gelation Conditions

To determine silk gelation under various sonication conditions, 0.5 ml of silk (water) solution in a 1.5 ml Eppendorf tube was sonicated with a Branson 450 ultrasonicator (Branson Ultrasonics Co., Danbury, Conn.), which consisted of the Model 450 Power Supply, Converter (Part No. 101-135-022), ½" Externally Threaded Disruptor Horn (Part No. 101-147-037), and ⅛" diameter Tapered Microtip (Part No. 101-148-062). The power output was varied from 10% to 50% amplitude (3 watts-21 watts) and sonication time was varied from 5 sec.-30 sec. To determine the effects of salts and pH on gelation, 0.5 ml of the silk solutions prepared as described above were sonicated at 20% amplitude (7 watts) and 15 sec. Solutions were incubated at 37° C. after sonication and the sol-gel transition was monitored visually by turning over the tube and checking the opacity change of the solution (Matsumoto et al.).

Based on preliminary results, silk fibroin concentrations up to 12% (w/v) were used to maintain lower viscosity, and the 12% solution gelled faster than the 8% and 4% samples. These results are set forth in Table 2, below.

TABLE 2

| | Gelation time for large volume (5 ml-7 ml) silk fibroin aqueous solution after sonication. | | | |
|---|---|---|---|---|
| | 7 W, 30 s | 10 W, 30 s | 15 W, 30 s | 21 W, 30 s |
| 4% (w/v) | No gel in 1 week | No gel in 1 week | 5 days | 12 hr (1 hr-2 hr after 2nd sonication) |
| 8% (w/v) | 6 day | 22-24 hr | 45-60 min | 15-30 min |
| 12% (w/v) | 4 day | 1.5-2 h | 15-30 min | gel in tube |

Note:
gelation time was estimated and averaged based on at least two independent experiments.

Example 4

Circular Dichroism (CD)

A 0.5 ml aliquot of 2% silk (water) solution was sonicated at 20% amplitude (7 watts) for 30 sec., and immediately loaded to a 0.01 mm path length, sandwich quartz cell (Nova Biotech, El Cajon, Calif.). CD measurement was conducted with a Jasco-720 CD spectrophotometer (Jasco Co., Japan).

All samples were scanned at 37° C. with a 4-s accumulation time at the rate of 100 nm/min, and the results were averaged from four repeated experiments. For the kinetic measurement of silk β-sheet structure formation, the ellipticity change at 217 nm was monitored for 2.5 hours with sampling every 10 sec.

Example 5

Mechanical Testing

A large volume of silk gel was prepared by sonication in order to accommodate mechanical testing. Silk solutions, 4%, 8%, and 12% (w/v) in glass flasks, were autoclaved 20 min. at 121° C. The autoclaved solution was supplemented with sterile Dulbecco's Modified Eagle Medium powder (DMEM powder, Invitrogen, Carlsbad, Calif.) and sodium bicarbonate (Sigma-Aldrich, St. Louis, Mo.) to a concentration of 0.135 g/ml and 0.037 g/ml, respectively. The resulting pH of the solution was pH 7.4, which was verified with a pH meter. A 7 ml aliquot was added to a 15 ml Falcon plastic tube and then sonicated at 20%, 30%, 40% amplitude (7 watts, 10 watts, 15 watts, respectively) for 30 sec. Six ml of the sonicated solution was added to small culture dishes (BD Falcon™, No. 35-3001, BD Biosciences, Palo Alto, Calif.) which were visually monitored in a 37° C. incubator, in order to approximate cell culture parameters, until gelation was complete based on opaque features and condensation on the gel surface. Subsequently, 9.525 mm diameter plugs (2 mm-3 mm in height) were punched out for mechanical tests immediately after gelation. The gel plugs were pre-conditioned in complete DMEM solution (Gibco/Invitrogen) for >1 hour prior to testing.

All samples were submerged in DMEM for storage and tested within 24 hours. Samples were evaluated on a 3366 Instron machine (Norwood, Mass.) equipped with unconfined compression platens and a 100N load transducer. The compressive extension method was employed with 1 mm/min rate of extension. The compressive stress and strain were determined and the elastic modulus was calculated based on a semi-automatic technique. The stress-strain diagram was segmented into eight sections below a cut-off stress level set beyond the initial linear portion of the diagram. Using least-squares' fitting, the highest slope among these eight sections was defined as the compressive modulus for the sample. The compressive strength was determined using an offset-yield approach. A line was drawn parallel to the modulus line, but offset by 0.5% of the sample gauge length. The corresponding stress value at which the offset line crossed the stress-strain curve was defined as the compressive strength of the scaffold. This testing was performed according to a modification based on the ASTM method F451-95.

Two unconfined compression testing regimes were pursued to evaluate the influence of sonication conditions on mechanical performance. First, strain-to-failure test was used to extract a traditional material stiffness property and to observe a failure response (Almany & Seliktar 26(15) Biomats. 2467-77 (2005); Kong et al., 24(22) Biomats. 4023-29 (2003)). Second, a stress relaxation test was used to evaluate equilibrium modulus properties, based on test parameters of Hung et al. (32 Ann. Biomed. Eng. 35-49 (2004)). Together, these measures provide broad comparisons against the published properties of other degradable hydrogels used for cell encapsulation. N=4 samples were evaluated for every group reported and were tested on a 3366 Instron machine (Norwood, Mass.) equipped with unconfined compression platens and 100 N load transducer and sample data exported using Bluehill Software Version 2.0.

For strain-to-failure testing, each sample was compressed at an extension-controlled rate of 1 mm/min, beginning after nominal tare loads were reached and sample heights recorded. The compressive stress and strain were determined by normalizing against sample geometries and the "traditional" elastic modulus was calculated as the slope of a tangency line established at the 5% strain portion of each stress/strain curve. The yield strength was determined by offsetting a line parallel to the tangency line by 2% strain; where the offset line intersected the stress/strain response was defined as the yield strength (which coincided with failure onset). For stress relaxation testing, samples were submerged in phosphate-buffered saline (PBS) and left under a nominal tare load for 200 s. Thereafter, samples were compressed at 1 mm/s until 10% strain was reached, which was held for 20 min. The equilibrium modulus was calculated by normalizing the relaxation stress by 10% strain.

Example 6

In Vitro Enzymatic Degradation of Silk Gels

Silk gel plugs (diameter=4 mm; height=2 mm-3 mm) at 4%, 8%, 12% (w/v) were prepared as described above and then immersed in 1 mL of Protease XIV (Sigma-Aldrich) solution in a 24-well plate. The protease solution was freshly prepared by dissolving the enzyme powder in PBS to reach a concentration of 5 U/mL and replaced with newly prepared solution every 24 hr. The control plugs were immersed in 1 mL of PBS which was also refreshed every 24 hr. All samples were incubated at 37° C. At days 1, 2, 3, 4 and 7, four plugs were washed with water, wiped with tissue paper to remove excess water on the gel surface, and weighed.

Example 7 hMSCs Seeding and Culturing in Silk Gels hMSCs were isolated from fresh whole bone marrow aspirates from consenting donors (Clonetic-Poietics, Walkersville, Md.) as described previously (Meinel et al., 71 J. Biomed. Mater. Res. A 25-34 (2004); Meinel et al., 88 Biotechnol. Bioeng. 379-91 (2004)), and culture expanded in a growth medium containing 90% DMEM, 10% fetal bovine serum (FBS), 0.1 mM non-essential amino acids, 100 U/mL penicillin, 1000 U/mL streptomycin, 0.2% fungizone antimycotic, and 1 ng/mL basic fibroblast growth factor (bFGF). Before use, passage 3-4 cells were trypsinized from culture flasks and resuspended in DMEM to obtain a cell density of $5 \times 10^7$ cell/mL. Fifteen mL of silk solution at 4%, 8%, and 12% (w/v) were steam sterilized (autoclaved) and supplemented with DMEM powder and sodium bicarbonate as described above. An aliquot of 5 mL was added to a 15-mL falcon plastic tube and a total of two tubes (control and cell seeded) were prepared for each silk concentration. A 4% (w/v) silk solution (5 mL) was sonicated in a laminar flow hood at 50% amplitude for 30 sec, and after 30 min incubation the solution was sonicated again under the same conditions. After the second sonication, the solution was cooled to room temperature within 5 min-10 min, and then 50 mL of the cell suspension was added and mixed with the sonicated silk solution to reach a final concentration of $5 \times 10^5$ cells/mL. The control sample was sonicated in the same way, but 50 mL of DMEM was added instead of the cell suspension after the sonication. An aliquot of 1.5 mL of the mixtures was quickly pipetted into 12-well cell culture plates, with a total of three wells prepared for each sample group. The 8% and 12% (w/v) solutions were sonicated once at 40% and 30% amplitude, respectively, for 30 s. A 50 ml aliquot of hMSC suspension was added and the mixture was plated as described above. All plates were then incubated at 37° C. and 5% $CO_2$.

Once the silk gelled in the plates within 0.5 hr-2 hr, small plugs (diameter=4 mm; height=2-3 mm) were punched out of the gels and placed in the wells of a new 24-well plate. The plugs were then cultured in 1 mL of growth medium containing 90% DMEM, 10% FBS, 0.1 mM nonessential amino acids, 100 U/mL penicillin, 1000 U/mL streptomycin, 0.2% fungizone antimycotic at 37° C. and 5% $CO_2$. For microscopy imaging, the hMSC encapsulated silk gels with a volume of 0.5 mL were prepared in 24-well plates and cultured in 1 mL of the same growth medium and under the same conditions as above, and images were taken at desired time points.

Example 8

Analyses of hMSCs Encapsulated in Silk Gels

Phase Contrast Microscopy—

At days 2, 6, 14 and 21 of culture, cell morphology was monitored by a phase contrast light microscopy (Carl Zeiss, Jena, Germany) equipped with a Sony Exwave HAD 3CCD color video camera.

Cell Proliferation—

Cell proliferation was assessed by DNA assay. Briefly, at each time point, 4 gel plugs from each group were washed with PBS, pH 7.4, weighed (wet weight), and chopped with microscissors in ice. DNA content (N=4) was measured using PicoGreen assay (Molecular Probes, Eugene, Oreg.), according to the manufacturer's instructions. Samples were measured fluorometrically at an excitation wavelength of 480 nm and an emission wavelength of 528 nm. DNA content was calculated based on a standard curve obtained in the same assay, and further normalized by the wet weight of each gel plug.

Cell Viability:

the viability of the hMSCs in the gel plugs was examined by a live/dead assay (Molecular Probes, Eugene, Oreg.). Briefly, at the end of culture, a gel plug of each group seeded with hMSCs were washed with PBS, cut into two halves, and incubated in 2 mM calcein AM (staining live cells) and 4 mM ethidium homodimer (EthD-1, staining dead cells) in PBS for 30 min at 37° C. The cross-section of the cut gel was imaged by Confocal microscopy (Bio-Rad MRC 1024, Hercules, Calif.) with Lasersharp 2000 software (excitation/emission ~495 nm/~515 nm). Depth projection micrographs were obtained from a series of horizontal sections, imaged at various distances from each other (1 μm-10 μm increments), based on the total height of a well-defined cell colony. Still images at various depths were captured and a series of micrographs were later combined for "z-stacked" compilation images.

Histology.

Silk gels seeded with cells were washed in PBS and fixed in 10% neutral-buffered formalin for 2 days before histological analysis. Samples were dehydrated through a series of graded ethanols, embedded in paraffin and sectioned at 5 mm thickness. For histological evaluation, sections were deparaffinized, rehydrated through a series of graded ethanols, and stained with hematoxylin and eosin (H&E).

Example 9

Statistics

Statistical analyses were performed using the Student's t-test. Differences were considered significant when pp0.05 and highly significant when pp0.01.

What is claimed is:

1. A process of rapidly forming silk fibroin gelation, comprising exposing silk fibroin to a treatment comprising ultrasonication for a sufficient period of time to initiate gelation, wherein power of ultrasonic waves is 3 watts to 21 watts and wherein substantial silk fibroin gelation forms less than 24 hours after the ultrasonication treatment.

2. The process of claim 1, wherein the silk fibroin gelation forms less than two hours after the ultrasonication treatment.

3. The process of claim 1, wherein the silk fibroin undergoes gelation at a time period ranging from about five minutes to about two hours after the ultrasonication treatment.

4. The process of claim 1, wherein the treatment further comprises a salt solution.

5. The process of claim 4, wherein the salt solution comprises ions selected from the group consisting of potassium, calcium, sodium, magnesium, copper, zinc, and combinations thereof.

6. The process of claim 5, wherein the salt is potassium, the salt concentration is less than 100 mM.

7. The process of claim 1, wherein the silk fibroin is in the form of an aqueous solution having a pH that is about pH 4 or lower or is about pH 7.5 or higher.

8. A method of controlling gelation time of silk fibroin by contacting a silk fibroin solution with an ultrasonication treatment for a period of time to initiate gelation, wherein power of ultrasonic waves is 3 watts to 21 watts and wherein substantial silk fibroin gelation forms less than 24 hours after the ultrasonication treatment.

9. The method of claim 8, wherein the silk fibroin gelation forms less than two hours after the ultrasonication treatment.

10. The method of claim 9, wherein the silk fibroin undergoes gelation at a time period ranging from five minutes to two hours after the ultrasonication treatment.

11. The method of claim 8, wherein the treatment further comprises a salt solution.

12. The method of claim 11, wherein the salt solution comprises ions selected from the group consisting of potassium, calcium, sodium, magnesium, copper, zinc, and combinations thereof.

13. The method of claim 12, wherein the salt is potassium, the salt concentration is less than 100 mM.

14. The method of claim 8, wherein the silk fibroin is in the form of an aqueous solution having a pH that is about pH 4 or lower or is about pH 7.5 or higher.

15. A method of encapsulating at least one agent in silk fibroin, comprising:
 (i)
  a. contacting a silk fibroin solution with an ultrasonication treatment for a sufficient period of time to initiate gelation, wherein power of ultrasonic waves is 3 watts to 21 watts and wherein substantial silk fibroin gelation forms less than 24 hours after the ultrasonication treatment; and
  b. introducing the agent(s) to the silk fibroin solution before substantial gelation occurs in the silk fibroin solution,
 thereby forming a silk-fibroin encapsulated agent; or
 (ii)
  a. introducing the agent(s) to a silk fibroin solution; and
  b. contacting a silk fibroin solution with an ultrasonication treatment for a sufficient period of time to initiate gelation, wherein power of ultrasonic waves is 3 watts to 21 watts and wherein substantial silk fibroin gelation forms less than 24 hours after the ultrasonication treatment, thereby forming a silk-fibroin encapsulated agent.

16. The method of claim 13, wherein the agent is a therapeutic agent or a biological material, or both.

17. The method of claim 13, wherein the agent is selected from the group consisting of cells, proteins, peptides, nucleic acids, PNA, aptamers, antibodies, hormones, growth factors, cytokines, enzymes, antimicrobial compounds, small molecules, drugs, and combinations thereof.

18. The method of claim 17, wherein said cell is a stem cell.

19. The method of claim 17, wherein a cell growth medium is introduced into silk fibroin with the biological material.

20. The method of claim 17, wherein the silk-fibroin encapsulated biological material is suitable for a biodelivery device.

* * * * *